United States Patent [19]

Walter

[11] Patent Number: 4,606,920

[45] Date of Patent: Aug. 19, 1986

[54] PHARMACEUTICAL COMPOSITION SUITABLE FOR TREATMENT OF INFLAMMATORY CHANGES OF THE BRONCHIAL MUCOSA

[76] Inventor: Hans-Peter Walter, Ludwig-Thoma-Strasse 29a, 8022 Grünwald, Fed. Rep. of Germany

[21] Appl. No.: 585,514

[22] Filed: Mar. 2, 1984

[30] Foreign Application Priority Data

Mar. 2, 1983 [DE] Fed. Rep. of Germany ....... 3307382

[51] Int. Cl.$^4$ ................... A01K 31/52; A01K 31/355; A01K 31/07
[52] U.S. Cl. .................................. 424/154; 514/263; 514/458; 514/725; 514/826
[58] Field of Search ............... 424/253, 154, 280, 284, 424/344; 514/263, 474, 458, 725, 826

[56] References Cited

U.S. PATENT DOCUMENTS 4,246,264  1/1981  Metz et al. ........................ 424/253

OTHER PUBLICATIONS

Remington's Phar. Sci., Mack Pub., 1980, pp. 949, 951, 955–956, 977, 809–813.
Merck Index, 9th Ed., Nos. 80, 3828 and 9004, 1976.
Unlisted Drugs, vol. 19, No. 5, May 1967, p. 61p.
Helwig, Modern Arzneimittel, 5. #d, pp. 875, 953, 1276 1980.
Negiver Organ.–Chem. Arzneimittel und Ahre Synonyma, vol. 1, 1978, pp. 109–110.
Schroeder, Arzneimittelchemie II, G. Thieme Stuttgart, 1976, pp. 66–67.

*Primary Examiner*—Stanley J. Friedman
*Assistant Examiner*—John W. Rollins, Jr.
*Attorney, Agent, or Firm*—John T. Roberts

[57] ABSTRACT

A pharmaceutical composition is being described that contains pharmacologically acceptable magnesium compounds, etofylline, vitamin A and vitamin C. It is especially suitable for treatment of inflammatory changes of the bronchial mucosa.

2 Claims, No Drawings

PHARMACEUTICAL COMPOSITION SUITABLE FOR TREATMENT OF INFLAMMATORY CHANGES OF THE BRONCHIAL MUCOSA

The invention concerns a pharmaceutical composition which is especially suitable for treatment of inflammatory changes of the bronchial mucosa.

BACKGROUND OF THE INVENTION

It is known that acute infections of the bronchial system differ fundamentally from chronic bronchitis. The cause of chronic bronchitis is not yet sufficiently clarified. For this reason, the World Health Organization defines chronic bronchitis as a disease that progresses at least over a period of two years with coughing and expectoration throughout at least three months of this period and on most days of the week.

Three forms can be differentiated from each other in the course of the disease. First there is an increased production in the bronchial system with productive coughing, then recurrent bacterial super-infections often ensue and finally flow impediments develope in the bronchi and bronchioles resulting in a chronic-obstructive bronchitis.

Pre-examinations have shown that a rise of the tissue histamine can be observed in inflammatory changes of the tracheobronchial system.

The possibilities of medicinal intervention in the histamine metabolism are manifold:

(a) For one, they exist with the known $H_1$ and $H_2$ receptor antagonists, which, howerver, as recognized, were not very successful in the treatment of acute or chronic lung diseases, specifically also of Asthma bronchiale (Ulmer et al., Reinhardt, Reinmann et al., 1982).

(b) Secondly, administering mast-cell membrane stabilizers that have found their permanent place in asthma therapy (Altunyan, 1981, Cox, Davis, Pepys et al., 1981).

(c) Thirdly, by intervention in the construction of histamine by blocking the conversion of histidine into histamine. The long-term administration of histidine decarboxylase blockers leads to a decrease of the tissue histamine also by test persons with healthy lungs (Reimann et al., 1982).

In the past various pharmaceutical compositions that intervene in the histamine metabolism were applied in the treatment of acute infections. Thereby, however, it was shown that blocking the histamine at the receptor does not lead to success.

SUMMARY OF THE INVENTION

The object of the invention is to provide a pharmaceutical composition for treatment of inflammatory diseases and changes of the bronchial mucosa which leads to a fast improvement of the disease.

This can be achieved by a pharmaceutical composition containing etofylline, vitamin A, one or more pharmacologically acceptable magnesium compounds and vitamin C and, if desired, usual auxiliary and/or carrier material.

Surprisingly, it was shown that a quick improvement of the general condition and simultaneously also a reduction of the tissue histamine resulted in patients having been given the pharmaceutical composition according to the invention.

DETAILED DESCRIPTION

The pharmaceutical composition according to the invention is a combination preparation that contains etofylline[7-(2-hydroxyethyl)-theophylline] and vitamins, especially high doses of vitamin A and/or lower doses of vitamin C, optionally together with vitamin E.

Suitable magnesium compounds that can be applied in the preparation according to the invention are usual magnesium compounds used in pharmacology, as e.g. magnesium salts with pharmacologically acceptable anions. Examples for specific magnesium compounds are: magnesium hydrogen-phosphate, magnesium glutamate, magnesium ascorbate, magnesium II amino acid chelates, magnesium gluconate, magnesium chloride, magnesium-hydrogen glutamate and magnesium orotate. Preferred magnesium compounds are magnesium hydrogen phosphate (e.g. as trihydrate) and magnesium-L-hydrogen-glutaminate.

Vitamin A (vitamin $A_1$ and/or vitamin $A_2$) can e.g. be added in the form of retinol palmitate. Vitamin E, α-tocopherole, known as the "antisterility vitamin" can be added e.g. as acetate.

The pharmaceutical composition according to the invention can preferably be formed for oral administration: for example to pills, dragées, powder, granules or capsules that contain all or single components of the combination preparation. For preparing the formulations, the ingredients are compounded in usual manner with known carrier and auxiliary substances. For preparing parenterally (e.g. introvenous) applicable preparations, usual solvents or emulgating liquids can be used. Further, it is possible to formulate concentrated preparations which can be diluted immediately before use.

The weight proportions of the single components can vary in a wide range and are not critical. They lie for example at 1 to 4 parts by weight of etofylline per part of weight of magnesium as magnesium ions.

The dosage depends on the patient and his state of health. The daily intake of magnesium should not exceed 10 mg/kg of body weight; vitamin A should be administered in a daily dosage not exceeding 50,000 I.U. A daily dosage of up to about 22,500 I.U. vitamin A, e.g. as retinol acetate, has been found as especially useful.

For example about up to 200 mg retinol plamitate can be administered daily. The daily dosage of etofylline in the combination according to the invention is preferably about 100-200 mg and especially up to about 150 mg. The daily dosage of vitamin C is about 50 mg to 200 mg and more.

A dosage unit form according to the invention, which e.g. can be administered once a day, can preferably contain (if administered two or three times a day the amounts of the components of the dosage unit can be divided by two or three):

Vitamin A: up to 50,000 I.U., preferably about 25,000 I.U. e.g. up to about 200 mg retinol palmitate;

Etofylline: 100-200 mg, e.g. about 150 mg;

Magnesium: up to 10 mg/body weight of the patient to be treated; i.e. about 50-70 mg magnesium; e.g. 250-300 mg magnesium hydrogen phosphate (preferably the trihydrate) together with 250-300 mg magnesium glutamate (e.g. as magnesium-L-hydrogen glutamate) or 400-600 mg, preferably about 500 mg magnesium orotate;

Vitamin C: at least about 50 mg, preferably 200 mg or more;

Vitamin E: about 30 mg up to about 100 mg as α-tocopherol acetate;
and optionally one or more of the following components:
Zinc oxide: 1-3 mg, e.g. 1.5 or 2.5 mg;
Methionine: 40-80 mg, e.g. 60 mg;
Mucolytic substance: e.g. ambroxole.HCl in an amount of 50 to 150 mg, e.g. about 100 mg.

Generally, the compositions of the invention can contain a mucolytic substance in a mucolytic effective amount, e.g. N-acetyl-L-cysteine (daily dosage about A100 to 300 mg) or ambroxole.HCl (trans-4-(2-amino-3,5-dibromobenzylamino)cyclohexanol HCl; daily dosage about 50 to 150 mg, e.g. 100 mg).

DESCRIPTION OF A PREFERRED EMBODIMENT OF THE INVENTION

A preferred embodiment of the pharmaceutical composition of the invention consists of a dose unit form containing:
  150 mg—etofylline
  22,500 I.U.—retinol palmitate
  30 mg—α-tocopherole acetate
  250 mg—magnesium hydrogenphosphate
  250 mg—magnesium glutamate
  50 mg—ascorbic acid
and if desired
  2.5 mg—zinc oxide.

Outstanding effects have been achieved with this combination. The combination can be formulated to dragées in accordance with usual pharmacological procedures. The etofylline, retinol palmitate and α-tocopherole acetate can be formulated separately from the magnesium compounds and ascorbic acid.

It has been found that the combination pharmaceutical composition according to the invention is especially suitable for treatment of inflammatory changes of the bronchial mucosa. This can concern changes or disease of the mucosa caused by smoking, occupational exposure to dust, vapors or gases, general air pollution, recurrent infections, bronchial allergies, climatic influences and chronic deforming bronchopathies. A main application purpose of the composition according to the invention lies in combating diseases of the bronchial mucosa caused by excessive nicotine, e.g. the so-called smoker's cough. Thereby the combination preparation according to the invention proved to be superior to the known histidine decarboxylase blockers. Surprisingly, the combination preparation effects a quicker improvement of the general state of health by simultaneous reduction of the tissue histamine.

The following examples explain the invention.

EXAMPLE 1

Formulation of a combination preparation for oral administration (as dragées):
  etofylline 150 mg
  retinol palmitate 22,500 I.U.
  α-tocopherole acetate 30 mg
  magnesium hydrogenphosphate 250 mg
  magnesium glutamate 250 mg
  zinc oxide (as usual additive) 2.5 mg
  ascorbic acid 50 mg

EXAMPLE 2

Formulation of a combination preparation for oral administration (in the form of two dragées):

Dragée 1
  magnesium hydrogenphosphate 250 mg
  magnesium glutamate 250 mg
  ascorbic acid 50 mg
  zinc oxide 2.5 mg Dragée 2
  etofylline 150 mg
  retinol palmitate 22,500 I.U.
  α-tocopherole acetate 30 mg

EXAMPLE 3

Formulation in the form of two dragées:

Dragée 1
  retinol palmitate 22,500 I.U.
  α-tocopherole acetate 30 mg
  etofylline 150 mg Dragée 2
  magnesium hydrogenphosphate 300 mg
  magnesium glutamate 300 mg
  ascorbic acid 50 mg

EXAMPLE 4

Pharmacological examination of the combination according to Examples 1 and 2:

Included in the examination were voluntary test persons of both sexes who had inhaled more than 25 cigarettes daily over a period of more than 4 years and who contiued this habit also during the test period.

The macroscopic inspection of the big bronchi with a fiber bronchoscope was applied as a hard criterion for an inflammatory change of the bronchial mucosa (score-classification 1-3 depending on the degree of severity). The microscopic examination was only considered to be a confirmation.

Doulbe blind and randomized, the test persons were administered either a HDC blocker or the combination preparation of Example 2.

Age Distribution of the Groups

Group I: HDC blocker, 30 test persons, average age 27 years (21-36 years)
Group II: Combination preparation according to the invention, 30 test persons, average age 30 years (26-39 years)

All test persons were fiber bronchoscopically examined at point 0, that is before taking the pharmaceutical composition. In each case two examiners diagnosed the macroscopic picture and made the classification of the degree of inflammation. In all cases several mucosa biopsies were taken from defined places for the histological and for the histamine and mast-cell examinations.

The test persons were instructed to take the specific composition of their group each morning and evening over a period of 14 days.

At the end of 14 days another fiber bronchoscopy was carried out with macroscopic, microscopic and histochemical examinations.

The histamine was determined fluorometrically according to the method of Lorenz et al., 1972, the mast-cell number with orthophthal dialdehyde according to the method of Reimann et al., 1980.

The statistical evaluation followed with the Student-t-Test for paired data and with the Wilcoxon-Rank-Sum-Test.

RESULTS

Before begin of the therapy all test persons showed macroscopically and histologically secured inflammatory changes.

Table 1 shows the distribution of inflammatory changes before treatment either with a HDC blocker (Group I) or with the combination preparation according to the invention (Group II).

The same table shows the change within the microscopic and macroscopic rating of the mucosa damage.

There is a distinct improvement of the condition of the damaged mucosa, the results of the combination preparation according to the invention being better than after giving the histidine carboxylase blocker.

Table 2 shows the subjective ailments present by the test persons before and after therapy.

Already after 8 days there was a subjective improvement of the named ailments such as coughing expectoration and retrosternal burning; thereby Group II fared better than Group I.

Already after 14 days over 90% of the test persons having taken the combination preparation according to the invention were relieved of discomfort, with those having taken the HDC blocker the percentage was only by about 65%.

TABLE 1

Macroscopic and histological valuation of the bronchial mucosa before and after treatment

| HDC-Blocker (I) | | | Combination Preparation (II) according to the invention | | |
|---|---|---|---|---|---|
| Score | before | after | Score | before | after |
| 0 | | 10 | 0 | | 18 |
| 1 | 7 | 14 | 1 | 4 | 10 |
| 2 | 17 | 5 | 2 | 16 | 2 |
| 3 | 6 | 1 | 3 | 10 | 0 |

TABLE 2

Subjective improvements of the ailments present by all test persons at the initial questioning: coughing, expectoration, scratching in the throat and retrosternal burning feeling

| Days | HDC-Blocker I (%) | Combination Preparation (II) according to the invention (%) |
|---|---|---|
| 8 | 50 | 82 |
| 14 | 64 | 90 |
| 28 | 72 | 92 |

The preparation according to the invention was well tolerated, several observed disagreeable reactions were insignificant.

The indication for a long-term treatment of patients with acute and chronic bronchial mucosa changes results on the basis of the favorable effect of the combination preparation according to the invention.

I claim:

1. A pharmaceutical composition in unit dosage form for the treatment of inflammatory changes and diseases of the bronchial mucosa comprising of between 100 and 200 mg of etofylline; vitamin A up to about 50,000 I.U. and between 50 and 70 mg of magnesium.

2. A method for treatment of inflammatory changes and diseases of the bronchial mucosa in humans comprising the administration to a human in need thereof of a daily dosage of about 200 mg of etofylline, up to 50,000 I.U. of vitamin A and about 70 mg of magnesium.

* * * * *